United States Patent
Tomiya et al.

[11] Patent Number: 6,094,263
[45] Date of Patent: Jul. 25, 2000

[54] VISUAL EXAMINATION APPARATUS AND VISUAL EXAMINATION METHOD OF SEMICONDUCTOR DEVICE

[75] Inventors: Hiroshi Tomiya, Tokyo; Eiji Isomura, Kanagawa, both of Japan

[73] Assignee: Sony Corporation, Japan

[21] Appl. No.: 09/083,540

[22] Filed: May 22, 1998

[30] Foreign Application Priority Data

May 29, 1997 [JP] Japan .................................. 9-139546
Feb. 20, 1998 [JP] Japan .................................. 10-038235

[51] Int. Cl.⁷ .......................... G01N 21/00; G01J 4/00
[52] U.S. Cl. .............................. 356/237.1; 356/240.1; 356/364
[58] Field of Search ................................ 356/364, 372, 356/376, 379, 383, 384, 385, 237.1, 240.1; 348/126

[56] References Cited

U.S. PATENT DOCUMENTS 5,298,989  3/1994  Tsukahara et al. ..................... 348/126
5,838,432  11/1998 Tokuhashi et al. ................... 356/139.03

*Primary Examiner*—Frank G. Font
*Assistant Examiner*—Michael Stafira
*Attorney, Agent, or Firm*—Rader, Fishman & Grauer; Ronald P. Kananen

[57] ABSTRACT

A visual examination apparatus for a semiconductor device for optically reading an image of a semiconductor device having a substantially rectangular package is disclosed, comprising:

four polarized light sources which are disposed so as to confront the four side surfaces of said package;

four reflection means each of which is disposed between each of said four polarized light sources and the corresponding side surface of said package, and reflects a projection image at each side surface side which is formed from polarized light emitted to said package from a polarized light source which said reflection means confronts through said package; and image reading means for collectively picking up projection images at the respective side surface sides which are reflected from said four reflection means and an image at the flat surface side of said package.

A visual examination method for a semiconductor device for optically reading an image of a semiconductor device having a substantially rectangular package is also disclosed.

8 Claims, 4 Drawing Sheets

VISUAL EXAMINATION APPARATUS AND VISUAL EXAMINATION METHOD OF SEMICONDUCTOR DEVICE

BACKGROUND OF THE INVENTION

The present invention relates to a visual examination apparatus and a visual examination method for a semiconductor device having a substantially rectangular package.

When a visual examination is performed on a semiconductor device comprising a QFP (Quad Flat Package) in which plural leads are extended from each side surface of a substantially rectangular package, it has been hitherto adopted that an image reading device such as a CCD camera or the like is disposed at the side of the package and the deformation of leads, the pitch between leads, and so forth are examined on the basis of the image of the side surface side of the package which is taken in by the image reading device.

In the semiconductor device visual examination based on the image reading device disposed at the side of the package as described above, an image on each of four side surfaces of the substantially rectangular package is picked up, and thus after an image on a first side surface is picked up, the package or the image reading device is rotated by 90° to pick up an image on a second side surface. This operation is repeated to pick up the respective images on the four side surfaces, and it is examined through predetermined image processing whether leads extending from each side surface are good or not.

Further, with respect to the warp, and so forth of the package, the outer dimension of the package is measured by using a laser measuring machine or the like, and the calculation is performed on the basis of the measurement result to determine the warp amount.

Recently, a BGA (Ball Grid Array) type semiconductor device in which a plurality of ball-shaped electrodes are arranged at the lower surface of a package and a CSP (Chip Size Package) type semiconductor device have been frequently utilized from the viewpoint of enhancement of mount density.

In such a BGA or CSP type semiconductor device, the ball-shaped electrodes are extended from the lower surface of the package. Therefore, reflection light from each electrode has a great effect, and thus it is very difficult to perform various examinations on the basis of pickup images. Particularly when a ball interval is examined, the ball and the package are slightly discriminated from each other on the basis of the pickup image, resulting in reduction in examination precision.

Further, there is a problem that the measurement of the outer dimension of the package on the basis of the laser measuring machine or the like needs a long processing time, and it is liable to be effected by the surface state of the package.

SUMMARY OF THE INVENTION

The present invention relates to a visual examination apparatus and a visual examination method for a semiconductor device which have been implemented to solve this problem. That is, the visual examination device for a semiconductor device according to the present invention optically reads an image of a semiconductor device having a substantially rectangular package, and includes four polarized light sources disposed so as to confront the four side surfaces of the package, four reflection means each of which is disposed between each of the four polarized light sources and the corresponding side surface of the package, and reflects a projection image at each side surface side which is formed from polarized light emitted to the package from a polarized light source which the reflection means confronts through the package, and image reading means for collectively picking up projection images at the respective side surface sides which are reflected from the four reflection means and an image at the flat surface side of the package.

The visual examination method for a semiconductor device according to the present invention comprises a step of irradiating polarized light to each side surface of the package, a step of picking up a projection image on each side surface of the package which is formed from incident polarized light, and a step of calculating the warp of the surface of the package on the basis of the projection image on each side surface of the package.

In the semiconductor device visual examination apparatus of the present invention, each of the four reflection means reflects the projection image at each side surface side which is formed by polarized light emitted from the polarized light source which confronts the reflection means through the package, so that the projection image which is independent of the surface state of the package can be obtained by the image reading means. Further, the projection images on the respective side surfaces of the package and the image on the flat surface of the package are collectively picked up, whereby the visual examination of the side surface sides and the visual examination of the flat surface side can be performed at the same time.

Further, in the semiconductor device visual examination method of the present invention, the projection image on each side surface of the package is picked by the image reading means, whereby the visual examination can be performed with no effect of the surface state of the package. Furthermore, the warp of the surface of the package can be examined by performing a predetermined calculation from the projection image on each side surface.

DETAILED DESCRIPTION OF THE PREFERRED EMBODIMENT

Figure 1A:
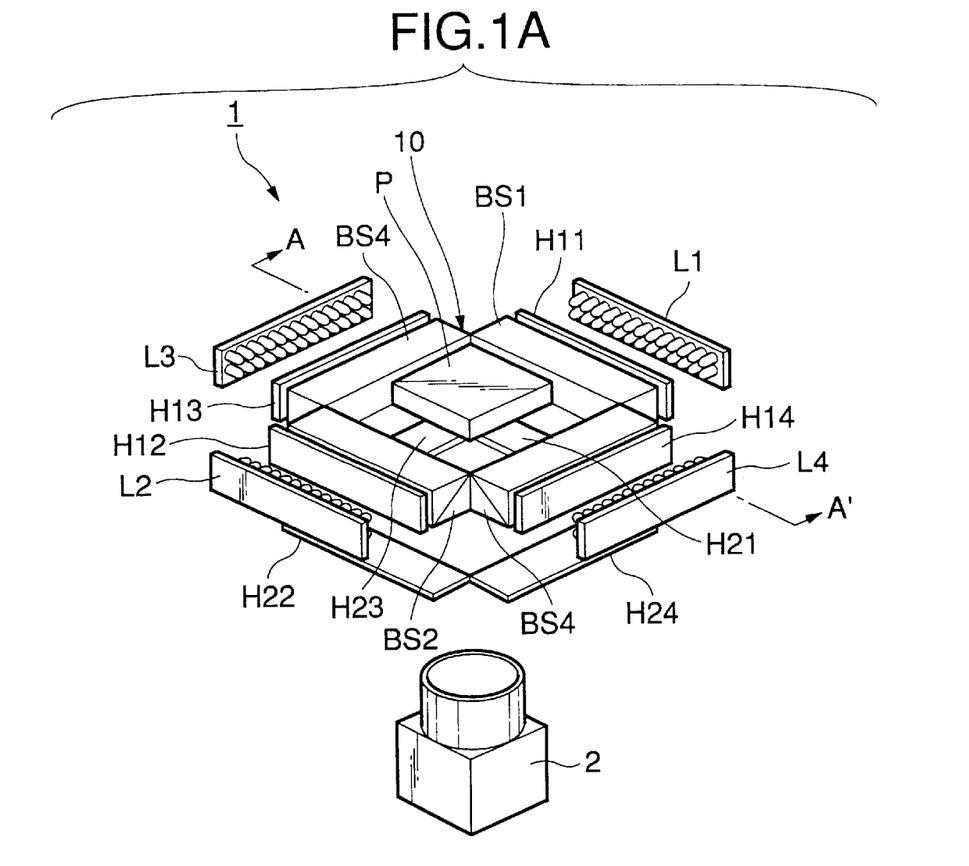
FIG. 1A and FIG. 1B are diagrams showing a visual examination apparatus according to an embodiment.
Figure 1B:
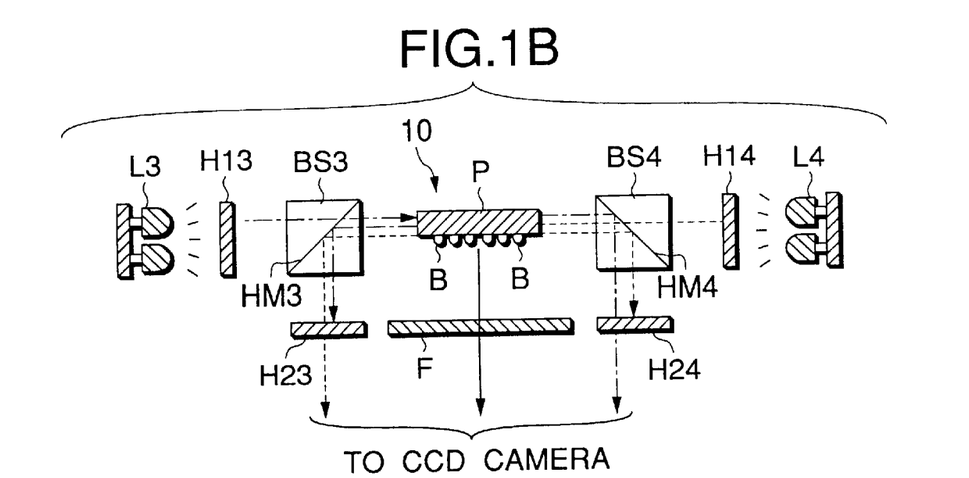

Embodiments of the visual examination apparatus and the visual examination method for a semiconductor device according to the present invention will be described with reference to the drawings. FIG. 1 is a diagram showing the visual examination apparatus of an embodiment, wherein FIG. 1A is a perspective view and FIG. 1B is a cross-sectional view taken along an arrow line A–A'.

In a visual examination apparatus 1 of this embodiment, an image of a semiconductor device 10 having plural ball electrodes B (see FIG. 1B) arranged in a grid form on the lower surface of a substantially rectangular package P is obtained by a CCD camera 2, and the outlook thereof is examined through image processing.

That is, the visual examination apparatus 1 includes four light sources L1 to L4 which are arranged so as to confront the four side surfaces of a package P of a semiconductor device 10, four polarizing plates H11 to H14 which are arranged between the respective light sources L1 to L4 and the respective side surfaces of the package P, four beam splitters BS1 to BS4 which are arranged between the respective polarizing plates H11 to H14 and the respective side surfaces of the package P, polarizing plates H21 to H24 which are arranged below the respective beam splitters BS1 to BS4, and a CCD camera 2 which is disposed at the lower side of the polarizing plates H21 to H24 and below the semiconductor device 10.

Of these elements, a polarized light source for emitting prescribed polarized light is constructed by the four light sources L1 to L4 and the polarizing plates H11 to H14 which are arranged in correspondence with the respective light sources L1 to L4.

The four light sources L1 to L4 comprise LED illumination which is constructed by plural LEDs (light emitting diodes), for example.

Each of the polarizing plates H11 to H14 polarizes the light emitted from each of the light sources L1 to L4 to generate polarized light having a predetermined polarization angle. The polarization angle of the polarized light generated by the polarizing plate H11, H12, H13, H14 is set on the basis of the relationship with the polarizing plate H12, H11, H14, H13 which are disposed at the facing side so as to interpose the package P therebetween. The polarized light thus generated will be described later.

Each of the beam splitters BS1 to BS4 has a half mirror, and it transmits therethrough about a half of the polarized light which is emitted from each of the light sources L1 to L4 and generated through each of the polarizing plates H11 to H14 and reflects therefrom about a half of the polarized light coming from the package P side.

The polarizing plates H21 to H24 which are disposed below the beam splitters BS1 to BS4 are used to select transmission or non-transmission of light reflected from the beam splitters BS1 to BS4.

The CCD camera 2 which is disposed below the semiconductor device 10 takes the light transmitted from the polarizing plates H21 to H24 and the reflected light from the lower surface of the semiconductor device 10 to convert the light to electrical signals.

In the visual examination apparatus 1 thus constructed, the projection image on each side surface of the package P of the semiconductor device 10 and the image of the lower surface of the package P can be collectively picked up mainly by the CCD camera 2.

That is, by setting the polarization angles of the polarizing plates H11 to H14 and the polarizing plates H21 to H24 described above, only the projection image of each side surface of the package P is transmitted as the image of the side surface to the CCD camera 2.

Here, the propagation of the light in the relationship between the polarizing plate H13, H14 and the polarizing plate H23, H24 will be described with reference to FIG. 1B.

First, the light emitted from the light source L3 is polarized into polarized light having a first polarization angle (see a one-dotted chain arrow of the figure) by the polarizing plate 13, and the light is transmitted through the half mirror HM3 of the beam splitter BS3 and reaches the left side surface of the package P of the semiconductor device 10 in the figure. A part of the polarized light having the first polarization angle impinges against and is reflected from the left side surface of the package P in the figure and the other does not impinge against the left side surface of the package P and propagates to the right side of the package P in the figure.

The polarized light of the first polarization angle which impinges against and is reflected from the left side surface of the package P, that is, the reflection image of the left side surface of the package P in the figure reaches the beam splitter BS3 again, is reflected downwardly from the half mirror HM3 and then reaches the polarizing plate H23. The polarization angle is set to the polarizing plate H23 so that the polarized light having the first polarization angle is not transmitted through the polarizing plate H23, and the polarized light having the first polarization angle which is reflected from the half mirror HM3 is intercepted by the polarizing plate H23. That is, the reflection image of the left side surface of the package P in the figure does not reach the CCD camera.

On the other hand, the polarized light having the first polarization angle which does not impinge against the left side of the package P and propagates to the right side of the package P, that is, the projection image of the right side surface of the package P reaches the beam splitter BS4, is reflected downwardly from the half mirror HM4 and then reaches the polarizing plate H24. The polarization angle is set to the polarizing plate H24 so that the polarized light having the first polarization angle is transmitted through the polarizing plate H24, and the polarized light having the first polarization angle which is reflected from the half mirror HM4 is transmitted through the polarizing plate H24. That is, the projection image of the right side surface of the package P in the figure reaches the CCD camera.

That is, the polarizing plate H13 and the polarizing plate H24 are set so that only the polarized angle having the same polarization angle is transmitted therethrough, and the polarizing plate H13 and the polarizing plate H23 are set so that polarized light having different polarization angles is transmitted therethrough, whereby the CCD camera can pick up the projection image of the right side surface of the package P to which the light from the light source is not irradiated.

Subsequently, the light emitted from the light source L4 is polarized into the polarized light having the second polarization angle (see a broken line arrow in the figure) by the polarizing plate 14, and it is transmitted through the half mirror HM4 of the beam splitter BS4 and then reaches the right side surface of the package P of the semiconductor device 10. A part of the polarized light having the second polarization angle impinges against and is reflected from the right side surface of the package P, and the other does not impinge against the right side surface of the package P and propagates to the left side of the package P.

The polarized light having the second polarization angle which impinges against the right side surface of the package P and is reflected therefrom, that is, the reflection image of the right side surface of the package P reaches the beam splitter BS4 again, is reflected downwardly from the half mirror HM4, and then reaches the polarization plate H24. The polarization angle is set to the half mirror HM4 so that the polarized light having the second polarization angle is not transmitted through the polarizing plate H24, and the polarized light having the second polarization angle which is reflected from the half mirror HM4 is intercepted by the polarizing plate H24. That is, the reflection image of the right side surface of the package does not reach the CCD camera.

On the other hand, the polarized light having the second polarization angle which does not impinge against the right side surface of the package and propagates to the left side of the package P, that is, the projection image of the left side surface of the package P reaches the beam splitter BS3, is reflected downwardly from the half mirror HM3, and then reaches the polarizing plate H23. The polarization angle is set to the polarizing plate H23 so that the polarized light having the second polarization angle is transmitted through the polarizing plate H23. The polarized light having the second polarization angle which is reflected from the half mirror HM3 is transmitted through the polarizing plate H23. That is, the projection image of the left side surface of the package P in the figure reaches the CCD camera.

That is, the polarizing plate H14 and the polarizing plate H23 are set so that only the polarizing light having the same polarization angle is transmitted therethrough, and the polarizing plate H14 and the polarizing plate H24 are set so that the polarized light having different polarization angles are transmitted therethrough, whereby the CCD camera can pick up the projection image of the left side surface of the package P in the figure to which the light from the light source L4 is not irradiated.

FIG. 1B shows the propagation of the light emitted from the light source L3 and the light source L4, and the same is applied to the light source L1 and the light source L2. Therefore, for the images of the side surfaces of the package P which can be obtained by the CCD camera, all the reflection images thereof are removed therefrom, and only the projection images remain.

The reflection light of the lower surface of the package P of the semiconductor device 10 (see a solid line arrow in the figure) reaches the CCD camera through a prescribed filter F. This filter F is used to reduce the light amount of the reflection light from the lower surface of the package P. That is, when the projection images of the right side surface and the left side surface of the package P described above and the reflection light (reflection image) from the lower surface of the package P are picked up at the same time, the light amount of the reflection light is reduced by the filter F so as to be matched with the light amount of each projection image, whereby the signal levels of the respective images thus taken can be matched with one another.

Figure 2:
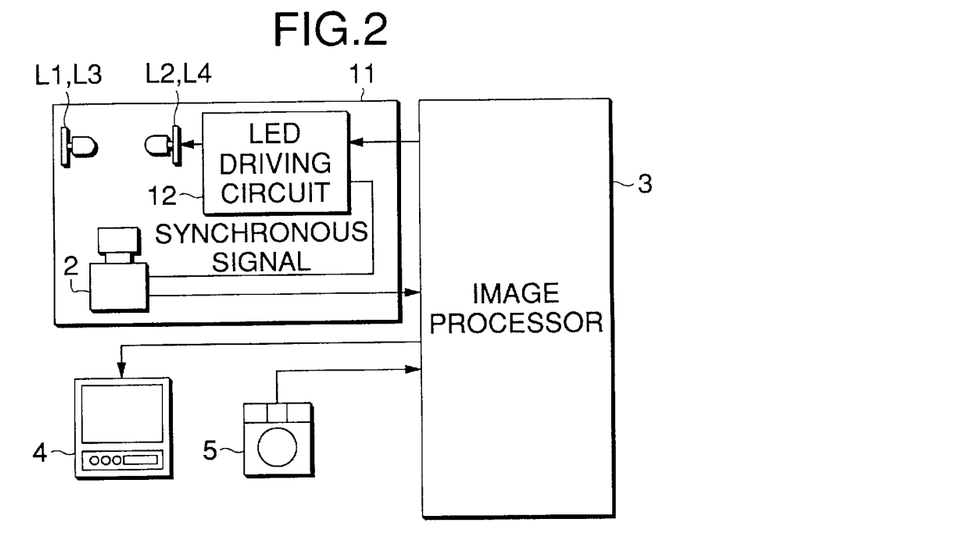
FIG. 2 is a diagram showing the system construction.

Next, the examination system using the visual examination apparatus will be described with reference to FIG. 2. That is, the visual examination apparatus 1 shown in FIG. 1 is installed as an examination unit 11 into this system. The polarizing plates H11 to H14, H21 to H24 and the beam splitters BS1 to BS4 as described above are not shown in FIG. 2, and they are disposed in the examination unit 11.

An LED driving circuit 12 is provided in the examination unit 11, and a synchronous signal is input to establish synchronization with the pickup of the image by the CCD camera 2. The CCD camera 2 of the examination unit 11 is connected to an image processor 3 to process an image which is picked up by the CCD camera 2, and perform the visual examination on prescribed items.

The image processor 3 is connected to an image display unit such as a monitor 4 or the like, and an input means such as a track ball 5 or the like. The image which is picked up by the CCD camera 2 and the image processed by the image processor 3 are displayed on the monitor 4. The track ball 5 is used to refer to the display content displayed on the monitor 4 for image processing and input prescribed information (the package type of the semiconductor device, the number of ball electrodes, and so forth) are input.

Next, a visual examination method for a semiconductor device which uses this examination system will be described with reference to the flowchart of FIG. 3. FIGS. 1 and 2 are referred to for reference numerals which are not illustrated in FIG. 3 insofar as they are not particularly indicated.

First, as shown in step S1, registration of the absolute plane is performed. The registration of the absolute plane is processing for picking up the image of the flat surface (absolute plane) serving as a reference for the arrangement of the semiconductor device 10 by the CCD camera 2 and stores it into the image processor 1. As the absolute plane is used a substantially rectangular plate (reference plate) having the same size as the package P of the semiconductor device 10, for example. The images of the respective side surfaces and the lower surface of the reference plate are picked up, and used as a reference when an image of the semiconductor device 10 is afterwards picked up and processed.

Subsequently, the image is picked up as shown in step S2. That is, the semiconductor device 10 is held by an absorbing holder or the like as not shown and disposed at the space surrounded by the respective light sources L1 to L4 (the space surrounded by the beam splitters BS1 to BS4 as shown in FIG. 1), and the image thereof is picked up by the CCD camera 2. When the image is picked up by the CCD camera 2, a synchronous signal which is matched with the pickup timing is supplied to the LED driving circuit 12, and light is irradiated from the light sources L1 to L4 to the semiconductor device 10 on the basis of the synchronous signal.

Figure 4:
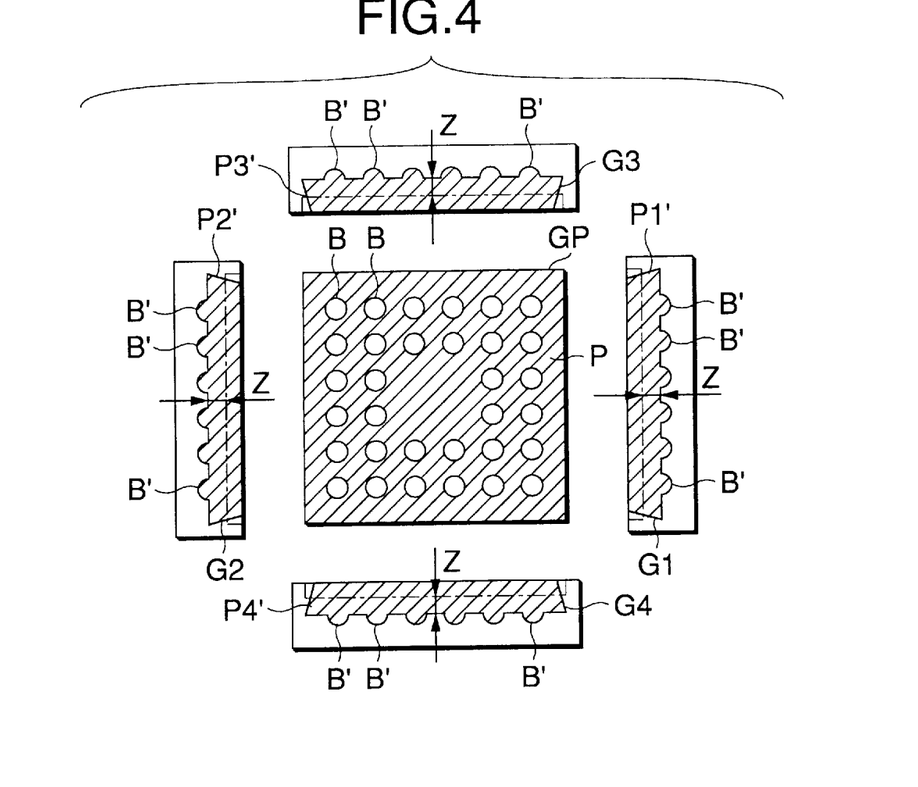
FIG. 4 is a diagram showing a pickup image.

FIG. 4 shows a pickup image. As described above, the CCD camera 2 can collectively pick up the projection image of each side surface of the package P of the semiconductor device 10 and the reflection image of the lower surface of the package P.

By the image pickup of the CCD camera 2, the reflection image GP of the lower surface of the package P and the projection images G1 to G4 of the respective side surfaces of the package P as shown in FIG. 4 are displayed on the monitor 4. A one-dotted chain line which is shown in conformity with the projection images G1 to G4 of the respective side surfaces indicates the position of the absolute plane which was previously registered.

The reflection image GP of the lower surface of the package P comprises the reflection image of the back surface of the package P and the plan-view images of plural ball electrodes B. The projection image G1 comprises the package side surface projection image P1' at the beam splitter BS1 side and the ball electrode projection images B' in FIG. 1, the projection image G2 comprises the package side surface projection image P2' at the beam splitter BS2 side and the ball electrode projection images B' in FIG. 1, the projection image G3 comprises the package side surface projection image P3' at the beam splitter BS3 side and the ball electrode projection images in FIG. 1, and the projection image G4 comprises the package side surface projection image P4' at the beam splitter BS4 side and the ball electrode projection images B' in FIG. 1.

Since the CCD camera 2 is disposed below the semiconductor device 10 as shown in FIG. 1, the projection images G1 to G4 which are actually reflected from the beam splitters BS1 to BS4 and then enter the CCD camera 2 are equivalent to projection images which are picked up from a slight slant (several angles to the horizontal direction) to an upper side of the package P. Accordingly, the projection images of the ball electrodes B disposed at the center portion of the package P are not displayed.

Subsequently, the warp of the package P is measured as shown in step S3. The warp of the package P is measured by a predetermined calculation using the respective package side surface projection images P1' to P4' which were previously picked up by the CCD camera 2.

Figure 5:
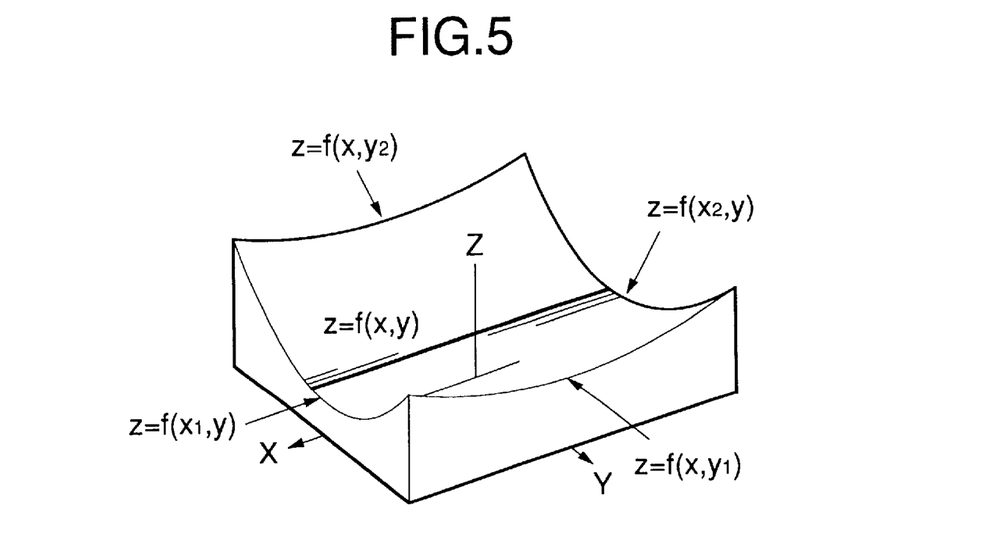
FIG. 5 is a diagram showing calculation of warp.

Here, the measurement method of the warp of the package P will be described. FIG. 5 is a diagram showing the calculation of the warp of the surface (package). That is, when the height direction to the flat surface of the package is set to Z and the direction of the flat surface is set to X, Y, the warp of the package is represented by a plane function $z=f(x,y)$. If the $f(x,y)$ is approximated by using a quadratic function, it is represented by the following equation (1):

$$f(x,y)=ax^2y+bxy^2+cx^2+dy^2+exy+fx+gy+h \quad (1)$$

Further, if the functions of the lines of the edges (lines indicated by arrows of FIG. 5) on the flat surface of the package P which correspond to the respective side surfaces are represented by $f(x,y1)$, $f(x1,y)$, $f(x,y2)$, $f(x2,y)$, the following equations (2) to (5) are obtained:

$$f(x,y1)=(ay1+c)x^2+(by1^2+ey1+f)x+(dy1^2+gy1+h) \quad (2)$$

$$f(x1,y)=(bx1+d)y^2+(ax1^2+ex1+g)y+(cx1^2+fx1+h) \quad (3)$$

$$f(x,y2)=(ay2+c)x^2+(by2^2+ey2+f)x+(dy2^2+gy2+h) \quad (4)$$

$$f(x2,y)=(bx2+d)y^2+(ax2^2+ex2+g)y+(cx2^2+fx2+h) \quad (5)$$

On the other hand, the height Z to the reference position of the edge (see the one-dotted chain line of FIG. 4) corresponding to the lower surface of the package P is calculated from the respective package side surface projection images P1' to P4' (see FIG. 4) on the basis of the images which are picked up by the CCD camera 2.

Here, the function of the height Z along the edges of the four side surfaces are represented by the following equations (6) to (9).

$$Z=A1x^2+B1x+C1 \quad (6)$$

$$Z=A2y^2+B2x+C2 \quad (7)$$

$$Z=A3x^2+B3x+C3 \quad (8)$$

$$Z=A4y^2+B4x+C4 \quad (9)$$

The equations (6) to (9) correspond to the above equations (2) to (5), and with this relationship the respective coefficients a to h in the equation (1) can be represented by the following equations (10) to (17).

$$a=(A1-A3)/(y1-y2) \quad (10)$$

$$b=(A2-A4)/(x1-x2) \quad (11)$$

$$c=(A3y1-A1y2)/(y1-y2) \quad (12)$$

$$d=(A4x1-A2x2)/(x1-x2) \quad (13)$$

$$e=((B1-by1^2)-(B3-by2^2))/(y1-y2) \quad (14)$$

$$f=((C2-cx1^2)y1-(C4-cx2^2)/(x1-x2) \quad (15)$$

$$g=((B4-ax2^2)x1-(B2-ax1^2)x2)/(x1-x2) \quad (16)$$

$$h=((C3-dy2^2)y1-(C1-dy1^2)/(y1-y2) \quad (17)$$

That is, the functions of the edges corresponding to the lower surface of the package P as shown in the above equations (6) to (9) are determined from the respective package side surface projection images P1' to P4' (see FIG. 4) which are picked up by the CCD camera 2, and the respective coefficients A1 to A4, B1 to B4, C1 to C4 are determined to determine the plane function $z=f(x,y)$ representing the lower surface of the package P, whereby the height at any position of the lower surface of the package P can be calculated and thus the warp examination can be performed.

Specifically, in each of the package side surface projection images P1' to P4' shown in FIG. 4, the value corresponding to the height Z from each reference position to the lower surface of the package is determined at plural positions for one side surface, and the coefficients A1 to A4, B1 to B4, C1 to C4 in the above equations (6) to (9) are calculated on the basis of this value. By using these coefficients A1 to A4, B1 to B4, C1 to C4, the coefficients a to h are determined from the above equations (10) to (17) to determine the plane function z f(x,y) of the lower surface of the package P.

Figure 3:
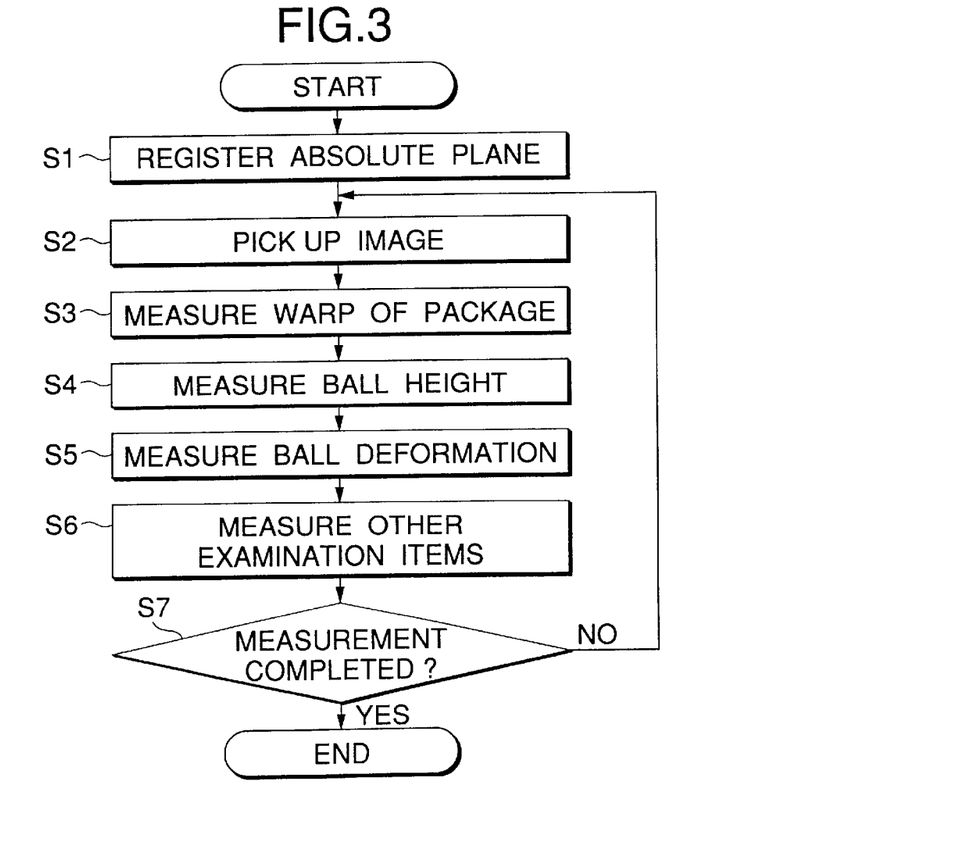
FIG. 3 is a measuring flowchart.

Here, in each of the package side surface projection images P1' to P4' shown in FIG. 4, the image of the absolute plane which is registered in step S1 of FIG. 3 is used for each reference position when the value corresponding to the height Z from each reference position to the lower surface of the package is determined at plural positions, whereby image reading errors due to the arrangement position precision of the respective beam splitters BS1 to BS4, the position of the CCD camera 2, and so forth and optical errors due to aberration of the lens system, etc. can be removed, and thus the examination can be performed with high precision.

Subsequently, the height of the ball electrodes B is measured as shown in step S4 of FIG. 3. The height of the ball electrodes is determined by calculating the diameter of each ball electrode B from the plan-view reflection image of the ball electrode B in the reflection image GP of the lower surface of the package P in the pickup images of FIG. 4, and setting about a half of the diameter as the height of the ball electrode B itself. That is, on the assumption that the ball electrodes B are spherical and they are fixed to the package P at the height corresponding to the half of the diameter, about a half of the diameter in the plan-view image is regarded as the ball electrode B itself.

The height of the ball electrode B itself is added with the warp of the package P to examine the height of the ball electrode B. That is, the height at the position of each ball electrode B is calculated from the plane function $z=f(x,y)$ representing the lower surface of the package P which is calculated in the previous step S3, and then added with the half of the diameter of the ball electrode B at the corresponding position, whereby the height of each ball electrode B which contains the warp of the package can be examined.

Subsequently, the deformation of the ball electrodes B is measured as shown in step S5 of FIG. 3. In this embodiment, when the deformation amount of the ball electrodes B is measured, "complexity" represented by the following equation (18) is first determined, and then "ball deformation degree" represented by equation (19), that is, the ratio of "complexity" to a circle (the shape of an ideal ball electrode) is calculated so that the ball deformation amount is expressed by a numerical value.

$$\text{"complexity"} = \text{(peripheral length of ball electrode)}/\text{(area of ball electrode in plain view)} \quad (18)$$

$$\text{"ball deformation degree"} = (\text{"complexity" of ball electrode})/ \quad (19)$$
$$(\text{"complexity" of circle})$$
$$= ((\text{radius of circle}) \times$$
$$(\text{"complexity" of ball electrode}))/2$$

As described above, the deformation amount of the ball electrodes B can be quantitatively examined on the basis of the numerical value of the "ball deformation degree".

Further, the other examination items (for example, damage, soil) are measured as shown in step S6 of FIG. 3, and then it is judged whether the measurement is completed or not as shown in step S7. If the judgment is Yes in step S7, the measurement is completed. On the other hand, when the measurement on a next semiconductor device 10 is continued, the judgment of the step S7 is No, and the steps S2 to S6 are repeated.

Figure 6:
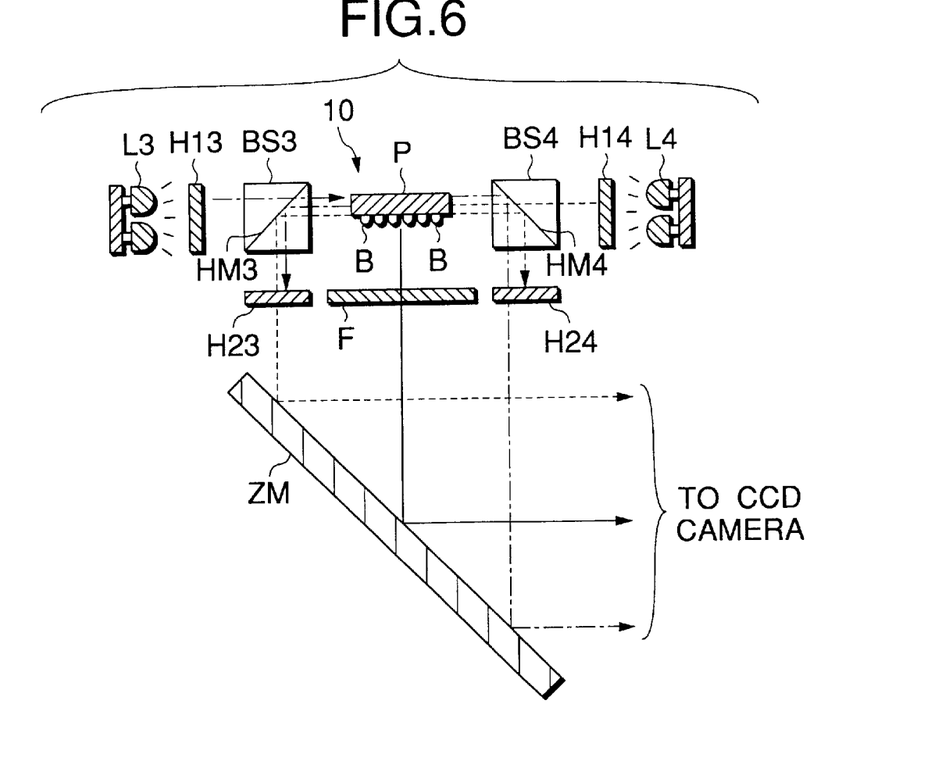
FIG. 6 is a cross-sectional view showing the main part of another embodiment.
Figure 7:
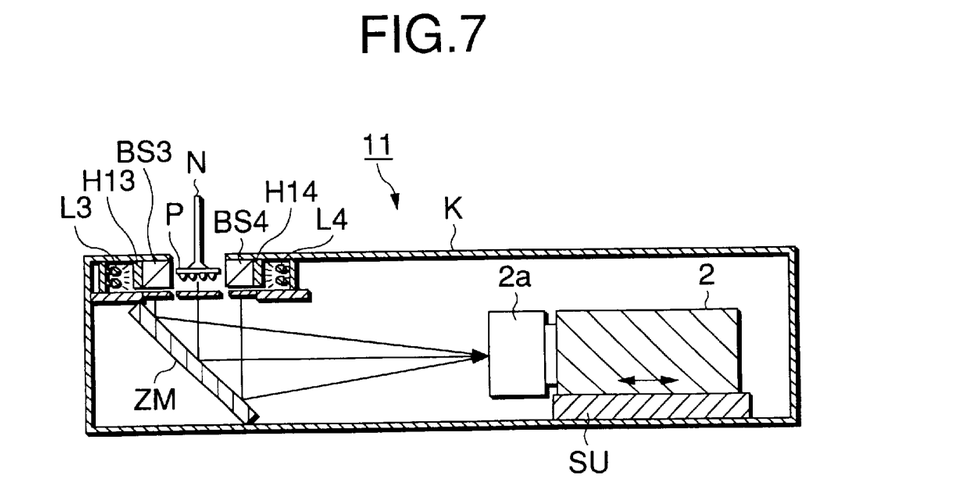
FIG. 7 is a cross-sectional view showing an examination unit to which the other embodiment is applied.

Next, another embodiment according to the present invention will be described. FIG. 6 is a cross-sectional view showing the main part of another embodiment, and FIG. 7 is a cross-sectional view of an examination unit to which the other embodiment is applied. That is, the visual examination apparatus in the embodiment shown in FIG. 6 is characterized in that projection images of side surfaces of the package P of the semiconductor device 10 and a reflection image of the lower surface of the package P are reflected in the lateral direction of the figure by an image reflection mirror ZM and then picked up by a CCD camera. In order to make it easy to understand the description, only the construction for picking up the projection images of the two sides of the package P of the semiconductor device 10 are illustrated. However, actually, the same construction is satisfied for the other two side surfaces in order to pick up the projections of the four side surfaces.

This visual examination apparatus includes light sources L3, L4 for irradiating light to the respective side surfaces of the package P, polarizing plates H13, H14 which are disposed between the light sources L3, L4 and the side surfaces of the package P, beam splitters BS3, BS4 disposed between the polarizing plates H13, H14 and the side surfaces of the package P, polarizing plates 23, 24 disposed below the beam splitters BS3, BS4, a filter F disposed below the package P, and an image reflection mirror ZM for reflecting the images passing through the polarizing plates 23, 24 and the filter F in the lateral direction of the figure.

That is, this embodiment is designed so that the construction of the embodiment described above is added with the image reflection mirror ZM.

In such a construction, the image projection of each side surface of the package P is reflected downwardly by each beam splitter BS3, BS4 in the figure and passes through the polarizing plate 23, 24 while the reflection image of the lower surface of the package P passes through the filter F and is reflected in the lateral direction by the image reflection mirror ZM. Accordingly, the image reflection mirror ZM is inclined at about 45 degrees to reflect the projection image of each side surface of the package P and the reflection image of the lower surface of the package P in the lateral direction of the figure.

Further, in this embodiment, a CCD camera is disposed at a reflection destination position by the image reflection mirror ZM. That is, this construction enables the apparatus to be laid out oblongly.

In the examination unit 11 to which this embodiment is applied as shown in FIG. 7, the construction of the light sources L3, L4, the polarizing plates H13, H14, the beam splitters BS3, BS4, and so forth and the image reflection mirror ZM and the CCD camera 2 are accommodated in the oblong housing K.

The CCD camera 2 is secured to a slide unit SU in the housing K so that the focusing point thereof is adjustable. Further, the housing K contains a light source control board, a driving linear motor for the slide unit SU, a driver circuit for driving a linear motor, and so forth as not shown.

In this examination unit 11, the package P of the semiconductor device is absorbed and held by an absorbing nozzle N of an absorbing robot or the like, and disposed between the beam splitters BS3, BS4. By irradiating light from the light sources L3, L4 in this state, the projection images of the respective side surfaces of the package P and the reflection image of the lower surface of the package P are reflected in the lateral direction of the figure by the image reflection mirror ZM disposed at the lower side, arrive at the CCD camera 2 through a lens 2a and are picked up as images.

By constructing such an oblong examination unit 11, it can be easily mounted on a handler which is an examination apparatus for a semiconductor device or a main base of in-line equipment, and maintenance such as positional adjustment of the CCD camera 2 (calibration adjustment), and so forth can be easily performed.

That is, the examination unit 11 is made oblong and thus the height thereof is reduced. Therefore, even when it is mounted on the handler or the main base of the in-line equipment, the overall height is not excessive, and the semiconductor device can be directly fed by an absorbing robot for semiconductor devices which is used for an apparatus for a handler or the like.

Further, when the oblong examination unit 11 is placed on the main base, the CCD camera 2 is also located at a near position (height) to the main base, and thus it is located at a near position to an operator who makes an adjustment or maintenance, whereby the maintenance work can be more enhanced.

In this embodiment, the projection images of the four side surfaces of the package P of the semiconductor device are picked up. However, when the visual examination is applied to a semiconductor device having leads extending from two side surfaces of the package P such as an SOP (Small Outline Package), the light sources, the polarizing plates and the beam splitters may be located at only the positions corresponding to the two side surfaces.

As described above, according to the visual examination apparatus and the visual examination method of the present invention, the following effects are achieved. That is, in the visual examination apparatus of the present invention, the projection images of the respective side surface of the package and the image of the flat surface side of the package are collectively picked up, whereby the visual examination of the side surface sides and the visual examination of the flat surface side can be performed simultaneously. Further, the projection image is picked up as an image of each side surface of the package, so that the image can be stably picked up without effecting the surface state, and the examination can be performed with high precision.

Further, in the visual examination method of the present invention, the examination of the surface side of the package can be performed with no effect of the surface state of the package, and the warp of the surface of the package can be examined by performing a predetermined calculation from the projection image on each side surface, so that the examination can be performed with high precision in a short time by the easy calculation.

What is claimed is:

1. A visual examination apparatus for a semiconductor device for optically reading an image of a semiconductor device having a substantially rectangular package, comprising:

four polarized light sources which are disposed so as to confront the four side surfaces of said package;

four reflection means each of which is disposed between each of said four polarized light sources and the corresponding side surface of said package, and reflects a projection image at each side surface side which is formed from polarized light emitted to said package from a polarized light source which said reflection means confronts through said package; and image reading means for collectively picking up projection images at the respective side surface sides which are reflected from said four reflection means and an image at the flat surface side of said package.

2. The semiconductor device visual examination apparatus as claimed in claim 1, further including image reflection means for laterally reflecting the projection images of the respective side surface sides reflected from said four reflection means and the image of the flat surface side of said package and transmitting said images to said image pickup means.

3. The semiconductor device visual examination apparatus as claimed in claim 1, further including a housing in which said two polarized light source, said four reflection means and said image pickup means are accommodated.

4. The semiconductor device visual examination apparatus as claimed in claim 2, further including a housing in which said two polarized light source, said four reflection means, said image pickup means and said image reflection means are accommodated.

5. A visual examination method for a semiconductor device for optically reading an image of a semiconductor device having a substantially rectangular package, comprising:

a step of irradiating polarized light to each side surface of said package;

a step of taking in a projection image on each side surface of said package which is formed from incident polarized light; and a step of calculating the warp of the surface of the package on the basis of the projection image on each side surface of said package.

6. The semiconductor device visual examination method as claimed in claim 5, wherein the image at the flat surface side of said package is collectively taken in together with the projection images on the respective surfaces of said package.

7. The semiconductor device visual examination method as claimed in claim 5, wherein an image serving as a reference for the arrangement of said package is taken in before the projection image on each side surface of said package is taken in.

8. The semiconductor device visual examination method as claimed in claim 6, wherein the shape of an electrode which is provided on the flat surface side of said package is examined on the basis of the image on the flat side surface of said package which is taken in by said image reading means.

* * * * *